United States Patent
Marmey et al.

(10) Patent No.: US 8,815,350 B2
(45) Date of Patent: Aug. 26, 2014

(54) METHOD FOR GRAFTING A POROUS ELEMENT FOR LEUCODEPLETION

(75) Inventors: Pascal Marmey, Linselles (FR); Emilie Bessy, Sainte Maxime (FR); Pierre Lutz, Bischheim (FR); Gregory Henard, Lille (FR)

(73) Assignees: Maco Pharma Societe Anonyme, Mouvaux (FR); Centre National de Recherche Scientifique, Paris (FR)

( * ) Notice: Subject to any disclaimer, the term of this patent is extended or adjusted under 35 U.S.C. 154(b) by 1035 days.

(21) Appl. No.: 12/337,715

(22) Filed: Dec. 18, 2008

(65) Prior Publication Data
US 2009/0159522 A1 Jun. 25, 2009

(30) Foreign Application Priority Data
Dec. 21, 2007 (FR) .................................... 07 09088

(51) Int. Cl.
*H05H 1/00* (2006.01)
*A61M 1/36* (2006.01)
*B05D 3/06* (2006.01)

(52) U.S. Cl.
CPC ............... *A61M 1/3633* (2013.01); *B05D 3/06* (2013.01)
USPC ........ 427/533; 210/335; 210/506; 210/502.1; 210/508; 210/435; 427/535

(58) Field of Classification Search
CPC ............ A61M 1/0209; A61M 1/0218; A61M 1/3633; B01D 39/14; B01D 39/16; B01D 29/00; B05D 7/02; B05D 3/06
See application file for complete search history.

(56) References Cited

U.S. PATENT DOCUMENTS

| 5,407,581 A | 4/1995 | Onodera et al. |
| 6,048,464 A | 4/2000 | Tanaka et al. |
| 2006/0073467 A1* | 4/2006 | Kuno et al. ........................ 435/2 |

FOREIGN PATENT DOCUMENTS

| EP | 0561379 A | 9/1993 |
| EP | 0606646 A | 7/1994 |
| EP | 0811412 A | 12/1997 |
| FR | 2892949 A | 5/2007 |

* cited by examiner

*Primary Examiner* — Dirk Bass
(74) *Attorney, Agent, or Firm* — Bachman & LaPointe, P.C.

(57) ABSTRACT

A method for grafting a porous element for leucodepletion by adsorption and/or filtration of a biological fluid, such as blood or a blood component, which method comprises the steps of impregnating the porous element with a solution containing a poly(ethylene oxide) having identical or different functional end groups; and applying an ionizing treatment to the impregnated porous element so as to ensure covalent cross-linking between the poly(ethylene oxide) and the porous element.

10 Claims, 3 Drawing Sheets

METHOD FOR GRAFTING A POROUS ELEMENT FOR LEUCODEPLETION

BACKGROUND (1) Field of the Invention

This invention relates to a method for grafting a porous element for leucodepletion, as well as the porous element obtained by this method, a filtration unit comprising such a porous element and a pouch system comprising such a filtration unit.

The invention typically applies to the filtration of blood or a blood component such as whole blood or packed red blood cells, as well as to the separation and collection of blood components, particularly in a closed circuit.

(2) Prior Art

Leukocytes have very significant undesirable effects, which has resulted in a search to eliminate them from the blood components intended for transfusion. As a matter of fact, leukocytes increase the risks of immune rejection, such as graft versus host disease, and promote the transmission of infectious agents.

In order to eliminate leukocytes from the blood components intended for transfusion, filtration units are already known, which comprise a casing containing a leucodepletion medium. In such units, the leucodepletion medium includes one or more membrane(s) and/or one or more layer(s) of a non-woven fabric made of a polymer material and treated so as to improve the leucodepletion rate, the recovery of the blood components, and the filtration priming time and/or filtration selectivity, e.g., by allowing the platelets to pass through.

For example, document EP-A1-0 606 646 describes a filtration unit the leucodepletion medium of which is coated with a polymer comprising basic functional groups and nonionic hydrophilic groups, such as poly(ethylene glycol) groups, the proportion between the basic groups and the hydrophilic groups being chosen so as to obtain a low rate of residual leukocytes and high-efficiency recovery of the red blood cells.

In this document, the coating is made in two steps. These steps consist in the radical copolymerization of a basic monomer and a hydrophilic monomer, and then simple impregnation of the filtration medium with a solution of the resulting copolymer. This means that the polymer coating is not covalently bonded to the leucodepletion medium, thereby causing a risk of elution of the copolymer into the filtrate. Furthermore, radical polymerization requires the use of a polymerization initiator, which may also end up in the filtrate, and which is not recommended.

In the same way, document US-20060207937 describes a filtration unit intended to eliminate the leukocytes from whole blood, which comprises a leucodepletion medium coated with a polymer obtained by reaction of a hydrophobic monomer and a hydrophilic monomer. Again, the polymer coating is not covalently bonded to the surface of the leucodepletion medium.

Finally, in document WO2007/054638, the leucodepletion medium of the filtration unit intended to eliminate the leukocytes by allowing the platelets to pass through is impregnated with a block copolymer consisting of a hydrophilic block of the poly(ethylene oxide) type and two hydrophobic blocks.

In all of these documents, it appears that the coating of a leucodepletion filter consists of a block copolymer comprising hydrophilic and non-hydrophilic portions.

SUMMARY OF THE INVENTION

Contrary to the teaching of prior art documents, the applicant has developed a method for grafting a porous element for leucodepletion by using a single hydrophilic polymer, without using any hydrophobic or basic polymer or block. Furthermore, the method enables irreversible grafting of the polymer onto the porous element.

In a surprising manner, a filtration unit comprising such a porous element possesses improved performance levels, such as a shorter priming time, a shorter filtration time and an improved recovery rate for the blood components of interest, while at the same time maintaining a good leukocyte retention rate.

According to a first aspect, the invention proposes a method for grafting a porous element for leucodepletion by adsorption and/or filtration of a biological fluid such as blood or a blood component, said method comprising the following steps providing for:

impregnating the porous element with a solution containing a poly(ethylene oxide) having identical or different functional end groups;

applying an ionizing treatment to the impregnated porous element so as to ensure covalent cross-linking between the poly(ethylene oxide) and said porous element.

According to a second aspect, the invention proposes a porous element for leucodepletion by adsorption and/or filtration of a biological fluid such as blood or a blood component, said element having been grafted together with poly(ethylene oxide) by implementing the method according to a first aspect of the invention, one end of said poly(ethylene oxide) being covalently bonded to said porous element.

A third aspect of the invention relates to a filtration unit for biological fluid such as blood or a blood component comprising an outer casing equipped with at least one inlet opening and at least one outlet opening, the casing containing a leucodepletion medium interposed between said openings, said leucodepletion medium comprising at least one porous element according to the second aspect of the invention.

Finally, the fourth and fifth aspects of the invention relate to a pouch system for leucodepletion of a biological fluid such as blood or a blood component, comprising a filtration unit according to the third aspect of the invention, which is connected or connectable to a collection pouch for the biological fluid.

BRIEF DESCRIPTION OF THE DRAWINGS

Other objects and advantages will become apparent from the following description.

DETAILED DESCRIPTION OF THE PREFERRED EMBODIMENT(S)

The invention proposes a method for grafting a porous element for leucodepletion by adsorption and/or filtration of a biological fluid such as blood or a blood component.

The porous element for leucodepletion by adsorption and/or filtration is, for example, formed from a porous or fibrous layer made of polyolefin, such as polypropylene, or of polyester, such as polyethylene terephthalate or polybutylene terephthalate.

The fibrous porous layer is, in particular, a layer of non-woven fabric of the melt-blown type.

In particular, the mean pore diameter of the porous element is between 3 and 20 μm.

This porous element is capable of eliminating the leukocytes from a biological fluid such as blood or a blood component. The blood component, in particular, is whole blood or packed red blood cells obtained from a whole blood donation.

In order to improve the hydrophily or blood compatibility of the leucodepletion porous element, the surface thereof can be coated with specific molecules or macromolecules which are then permanently bonded so as to prevent salting-out into the blood products.

According to the invention, the porous element is grafted according to a method comprising the steps consisting of:
impregnating the porous element with a solution containing a poly(ethylene oxide) having identical or different functional end groups;
applying an ionizing treatment to the impregnated porous element so as to ensure covalent cross-linking between the poly(ethylene oxide) and said porous element.

Figure 3:
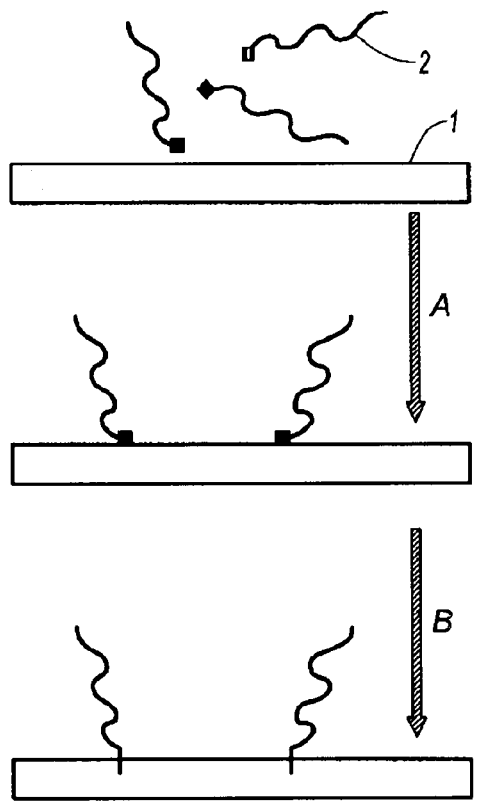
FIG. 3 is a schematic representation of the steps of grafting a porous element together with a methoxypoly(ethylene oxide) monomethacrylate.

FIG. 3 is a schematic representation of the steps of this method wherein a porous element 1 is grafted together with a poly(ethylene oxide) 2 by means of an impregnating A and grafting B step.

The poly(ethylene oxides) usable for the invention are hydrophilic and have a linear or branched structure, and are advantageously branched. For example, the poly(ethylene oxide) has the formula $R_1-(CH_2-CH_2-O)_{n-1}-CH_2-CH_2-R_2$ (I), wherein n is an integer greater than or equal to 2 and $R_1$ and $R_2$ represent identical or different functional groups. In particular, $R_1$ and $R_2$ represent a functional group chosen from among a hydroxy or an alkoxy, e.g., a methoxy, phenoxy, benzoxy or end group which is capable of being polymerized by an ionizing treatment.

Specific polymers are methoxypoly(ethylene oxide) of formula (I), wherein $R_1$ is methoxy and $R_2$ is hydroxy or dimethoxypoly(ethylene oxide) of formula (I), wherein $R_1$ and $R_2$ are methoxy.

Other specific polymers are the macromonomers of poly(ethylene oxide), in particular those of formula (I), wherein at least one of $R_1$ or $R_2$ is an end group capable of being polymerized by an ionizing treatment.

The macromonomers are polymers or oligomers having a reactive end group, e.g., a polymerizable functional group, which enables it to react like a monomer.

The poly(ethylene oxide) macromonomer according to the invention includes an end group which is capable of being polymerized by an ionizing treatment. This polymerizable group promotes covalent cross-linking with the porous element.

Examples of end groups capable of being polymerized by an ionizing treatment are an acryloyloxy, a methacryloyloxy, an acrylamido, a methacrylamido, a vinyloxy or an allyloxy.

The end of the poly(ethylene oxide) macromonomer carries either a non-polymerizable group such as an alkoxy, e.g., a methoxy, phenoxy or benzoxy, or a group capable of being polymerized by an ionizing treatment, which may or may not be the same as the one carried at the first end.

Figure 1:
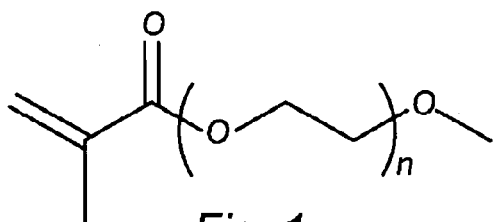
FIG. 1 shows the chemical structure of a methoxypoly(ethylene oxide) monomethacrylate, wherein n is an integer greater than or equal to 2.

A specific family of poly(ethylene oxide) macromonomers is shown in FIG. 1, by the semi-structural formula thereof, wherein n is an integer greater than or equal to 2. These macromonomers include an oligomer or polymer of poly(ethylene oxide) having, at one of the ends thereof, a methacrylate as the polymerizable group, and, at the other end thereof, a methoxy group.

These poly(ethylene oxide) macromonomers possess important properties. As a matter, the poly(ethylene oxide) polymer portion possesses both blood compatibility and hydrophilic properties, and the methacrylate function can be activated by the addition of energy so as to enable covalent cross-linking of the macromonomer on the leucodepletion porous element.

Specific examples of poly(ethylene oxide) macromonomers are the hydroxypoly(ethylene oxide) monomethacrylates of formula (I), wherein $R_1$ is hydroxy and $R_2$ is methacryloyloxy, the poly(ethylene oxide) dimethacrylates of formula (I), wherein $R_1$ and $R_2$ are methacryloyloxy, and the methoxypoly(ethylene oxide) monomethacrylates of formula (I), wherein $R_1$ is methoxy and $R_2$ is methacryloyloxy.

Methoxypoly(ethylene oxide) monomethacrylates are available commercially (Sigma-Aldrich).

Figure 2:
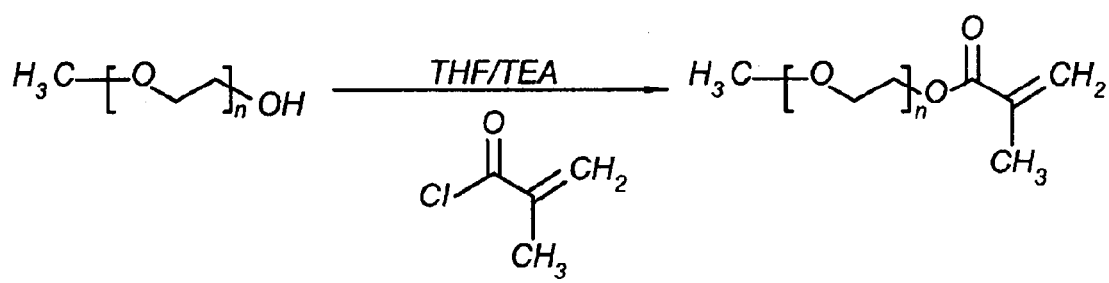
FIG. 2 shows a schematic diagram of the synthesis of a methoxypoly(ethylene oxide) monomethacrylate from a methoxypoly(ethylene oxide).

Methoxypoly(ethylene oxide) monomethacrylates and poly(ethylene oxide) dimethacrylates can be synthesized from hydroxy, methoxypoly(ethylene oxide) and dihydroxypoly(ethylene oxide), respectively, via reaction with a methacryloyl chloride in a tetrahydrofuran solvent in the presence of triethylamine (FIG. 2 in relation to the methoxypoly(ethylene oxide) monomethacrylates).

Another synthetic pathway is described in the document Biomacromolecules 2004, 5, 1280-1287. Briefly, and in relation to poly(ethylene oxide) dimethacrylate having a molecular weight of 2960 g/mol, the synthesis is as follows: to a solution of 10 g (3.4 mmol) of 2960 g/mol purified poly(ethylene oxide) in 50 ml of dichloromethane are added 0.7 ml (4.8 mmol, 0.7 Eq per OH) of triethylamine and 1.2 ml (7.4 mmol, 1.1 Eq per OH) of 94% methacrylic anhydride. The reaction mixture is left under agitation and at ambient temperature for 4 and a half days. Purification is carried out by filtration over neutral alumina (dichloromethane/methanol gradient elution: 70/30 to 50/50). The solvents are evaporated and the residue is dissolved at 30° C. in 80 ml of dimethyl sulfoxide. The macromonomer is then precipitated from the solution thereof at ambient temperature and under agitation in 1.2 l of ether, then washed with ether prior to being filtered over sintered glass (porosity of 4). The end product, 9.5 g of a white solid, is recovered after drying under a vacuum, in an oven, to constant weight.

The methoxypoly(ethylene oxide) and methoxypoly(ethylene oxide) monomethacrylates are water-soluble, which facilitates the handling thereof.

In particular, the molecular weight of the poly(ethylene oxide) is greater than or equal to 500 g/mol, and in particular between 800 and 2000 g/mol.

Below 500 g/mol, poly(ethylene oxides) are generally toxic and not recommended for contact with blood or a blood component.

Above 5000 g/mol, the pendant chain of the poly(ethylene oxide) grafted to the surface of a porous element forms a random-coil which possesses a steric repulsion capability. This reduces the adsorption of the proteins and cells at the surface of the porous element, including that of the leukocytes.

The impregnating solution is a mixture consisting of a poly(ethylene oxide) as the solute and an aqueous and/or organic liquid as the solvent. It contains a low concentration of poly(ethylene oxide). In particular, the poly(ethylene oxide) is dissolved in a solvent at concentrations of between 0.01 and 5% by weight, and in particular between 0.1 and 2% by weight.

The impregnation solvents are, in particular, water, ethanol and acetone, either pure or mixed in various proportions. Water has an advantage over the organic solvents in that it is non-toxic.

Figure 4:
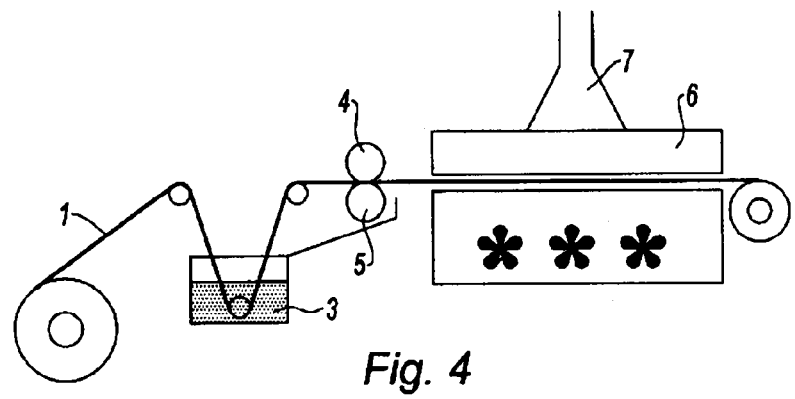
FIG. 4 is a schematic representation of piece of equipment enabling impregnation of a porous element according to the pad-dry principle.

The impregnation operation is carried out according to a pad-dry principle, e.g., with equipment shown in FIG. 4. The porous element 1 is soaked in a solution 3 of poly(ethylene oxide). The surplus of solution impregnated into the porous element 1 is then expressed or squeezed out by passing between two rollers 4, 5, the pressure of which is between 1 and 5 bars. Then, the porous element 1 is conveyed into an oven 6 equipped with mechanical ventilation 7, in order to dry it by evaporating the solvent. The speed, between 1 and 10 m/min, is regulated according to the nature and amount of solvent removed by the porous element.

A removal rate is determined by weighing the porous element before impregnation and after impregnation and drying, according to the following formula.

> Removal rate (%)=(Weight of impregnated and dried porous element−Weight of porous element before impregnation))/Weight of porous element before impregnation.

In particular, the removal rate is between 0.1 and 5% by weight of the porous element.

The poly(ethylene oxide) is then covalently bonded to the porous element by applying an ionizing treatment.

In the case where the poly(ethylene oxide) is a poly(ethylene oxide) macromonomer, the macromonomer is grafted to the porous element in order to obtain the covalent cross-linkage. Polymerization is carried out, in particular, by activating the polymerizable end group of the macromonomer. This is obtained, for example, by applying a ionizing treatment to the impregnated porous element.

The ionizing treatment contributes the energy sufficient to cause the rupture of a chemical bond and to create a new one. It may be of various types, such as a plasma treatment using a gas such as argon, nitrogen or oxygen, or else exposure to ionizing radiation or electron beams such as gamma or beta rays.

The purpose of the activation operation is to covalently surface-graft the poly(ethylene oxide) so as to immobilize it and to prevent the poly(ethylene oxide) polymer from salting-out into the filtered fluid passing through the blood product in the filtration unit.

The grafting method advantageously does not include any step for pre-radiating the porous element. As a matter of fact, this step is not required for grafting and impregnating a poly (ethylene oxide).

Figure 5:
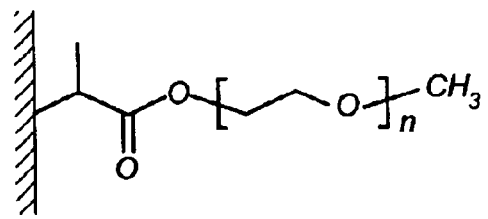
FIG. 5 is a schematic representation of the structure of a methoxypoly(ethylene oxide) monomethacrylate grafted to the surface of a porous element.

FIG. 5 shows the chemical structure of a poly(ethylene oxide) macromonomer once it has been grafted onto the porous element.

In order to monitor the efficiency of the grafting method, soxhlet extractions are carried out on samples at various steps of the grafting operation. Extraction from the porous element after the ionizing treatment enables determination of the extractible contents in the untreated porous element. Extraction from the impregnated porous element before and after the ionizing treatment enables determination of the effectiveness of such a treatment.

The grafting rate is then determined using the following formula:

> Grafting rate=(weight of extractable material without Treatment−weight of extractable material after Treatment/Weight of porous element without treatment Efficiency is then calculated using the following formula:

> Grafting efficiency=grafting rate/removal rate

The method according to the invention enables obtainment of a grafting efficiency of greater 70%.

According to a second aspect, the invention proposes a porous element for leucodepletion by adsorption and/or filtration of a biological fluid such as blood or a blood component, said element having been grafted together with a poly (ethylene oxide) by implementing the method according to the first aspect of the invention, one end of said poly(ethylene oxide) being bonded covalently to said porous element.

This porous element grafted together with the poly(ethylene oxide) has a critical wetting surface tension (CWST) of between 80 and 110 mN/m.

This CWST is determined by the method described in document WO-8903717.

This very high CWST of greater than 72 mN/m demonstrates the high hydrophily of the leucodepletion porous element, i.e., it can be wetted with water. The wettability of the thus improved porous element results in shorter filtration priming times than with non-grafted porous elements.

Surprisingly, despite this high wettability, the leucodepletion rate of a filtration unit comprising a grafted porous element such as this is substantially the same as with a filtration unit comprising a non-grafted porous element.

According to a third aspect, the invention relates to a filtration unit for a biological fluid such as blood or a blood component. The blood component, in particular, is whole blood or packed red blood cells obtained from a whole blood donation.

The filtration unit includes an outer casing equipped with at least one inlet opening and one outlet opening, the casing containing a leucodepletion medium interposed between said openings so as to form an inlet compartment for the fluid being filtered and an outlet compartment for the filtered fluid. The leucodepletion medium includes at least one porous element grafted together with a poly(ethylene oxide).

According to one particular embodiment, the filtration unit further includes a pre-filter and/or post-filter which are made in the form of at least one layer of non-woven fabric and which are arranged at the upstream side and downstream side of the leucodepletion medium, respectively.

These pre-filters or post-filters, in particular, have an average pore size greater than that of the leucodepletion medium, e.g., between 25 and 50 μm.

This filtration unit is used for the leucodepletion of a blood product, in particular depleted packed red blood cells, i.e., prepared by hard centrifuging of a unit of whole blood.

To accomplish this, the filtration unit is integrated into a pouch system.

Figure 6:
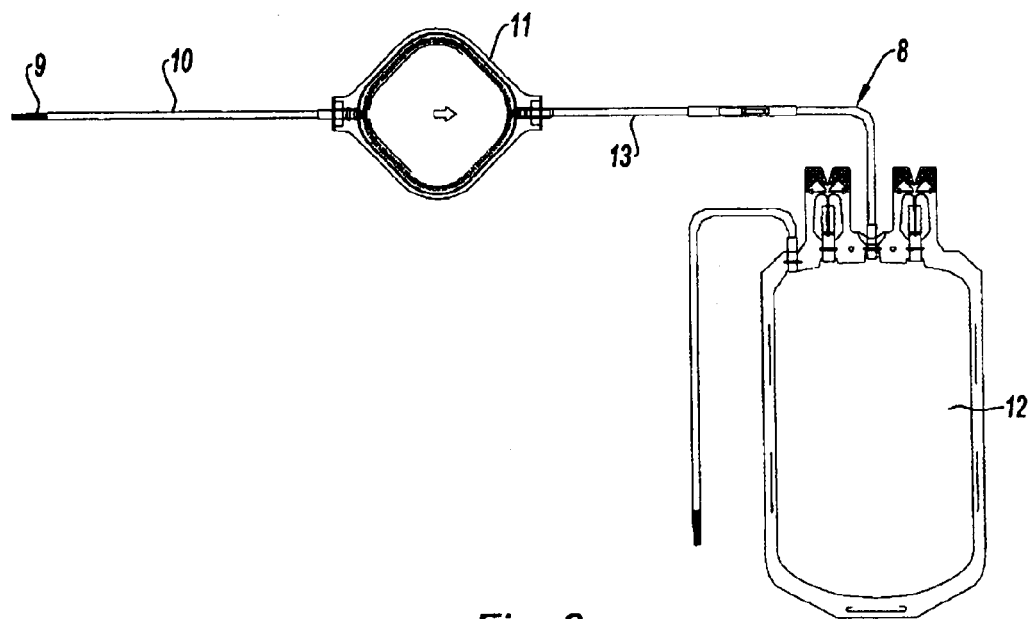
FIGS. 6 and 7 are each schematic representations of a pouch system comprising a filtration unit according to the invention.

In relation to FIG. 6, and according to a fourth aspect, the invention proposes a pouch system 8 for leucodepletion of a biological fluid, comprising:

a connector 9 intended to be connected to a collection pouch containing the biological fluid being filtered, said connector being connected, by means of tubing 10, to an inlet opening of a filtration unit 11 according to the invention; and a filtrate collection pouch 12, said pouch being connected, by means of tubing 13 and at the level of an inlet opening, to an outlet opening of the filtration unit.

Figure 7:
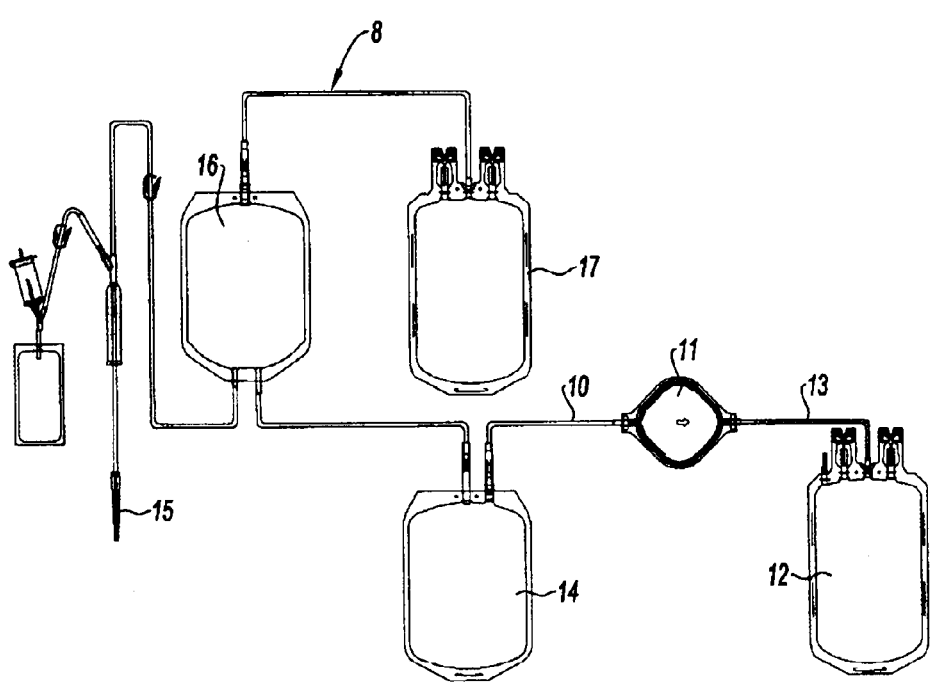

As an alternative, shown in FIG. 7, and according to another aspect of the invention, the pouch system 8 includes:
- a collection pouch 14 for the biological fluid, said pouch being connected, by means of tubing 10, and at the level of an outlet opening, to an inlet opening of a filtration unit 11 according to the invention, and
- a filtrate collection pouch 12, said pouch being connected, by means of tubing 13, and at the level of an inlet opening, to an outlet opening of said filtration unit 11.

In this alternative, the pouch system can likewise include blood sampling means, such as a needle, as well as secondary pouches 16, 17 joined together via tubes for separating and collecting whole blood and the components thereof.

Either of the pouch systems is used to filter packed red blood cells obtained by centrifuging a unit of whole blood. A preservative solution (SAGM, PAGAM) is advantageously placed inside the filtrate collection pouch 12.

According to one particular embodiment, prior to carrying out the filtration, the preservative solution is transferred extemporaneously, through the filtration unit 11, to the collection pouch 14 containing the packed red blood cells, so as to pre-wet the leucodepletion medium and dilute the packed red blood cells. Filtration of the packed red blood cells together with the preservative solution can then begin.

The leucodepletion medium of the filtration unit thus remains in the dry state until the use thereof.

EXAMPLES

Preparation of the Impregnating Solutions

The methoxypoly(ethylene oxide) monomethacrylates having a molecular weight of 300, 475 and 1100 g/mol (Sigma-Aldrich) and the dimethoxypoly(ethylene oxide) having a molecular weight of 1000 g/mol (Sigma-Aldrich) are used as is. The methoxypoly(ethylene oxide) monomethacrylates having a molecular weight greater than 1100 g/mol were synthesized at the Institute Charles Sadron of the CNRS, by functionalizing methoxypoly(ethylene oxide) (FIG. 2).

The methoxypoly(ethylene oxide) monomethacrylates or the dimethoxypoly(ethylene oxide) are dissolved in three types of solvents: water, an ethanol/water mixture in various ratios (V/V), and an ethanol/acetone mixture in various ratios (V/V).

The following solutions were prepared:

|  | Solvent | Concentration |
|---|---|---|
| Solution 1 | Water | 0.5% |
| Solution 2 | Ethanol/water (20/80) | 0.2% |
| Solution 3 | Ethanol/water (50/50) | 0.2% |
| Solution 4 | Ethanol/water (20/80) | 0.5% |
| Solution 5 | Ethanol/water (50/50) | 0.8% |
| Solution 6 | Ethanol/acetone (50/50) | 1% |

Impregnation

Two types of layers of a poly(butylene terephthalate) nonwoven fabric were modified by grafting a methoxypoly(ethylene oxide) monomethacrylate having a molecular weight of 1100 g/mol.

|  | Type 1 | Type 2 |
|---|---|---|
| Average fiber size (µm) | 1-2 | 1-2 |
| Air permeability (l/m²/s – 196 Pa) | 120-140 | 260-300 |
| Average pore size (µm) | 8-10 | 15-20 |
| Average thickness (µm) | 220-280 | 220-280 |

The two types of layers were impregnated according to the pad-dry principle, as described above, using the solutions as prepared above.

The removal rate obtained is between 0.4% and 1.2%.

Grafting

Grafting of the impregnated layers of type 1 and 2 above was carried out by a plasma treatment under the following conditions:

The plasma treatment is carried out on high-frequency discharge plasma. The plasma is generated in an enclosure at reduced pressure ($10<P<250$ mTorr). The generator power is between 300 and 1400 W. The gas used is an inert gas with a flow rate of between 0.1 and 2 l/min. The treatment time (dwell time in the plasma) is between 20 seconds and 2 minutes.

After grafting, the CWST of the layer is between 90 and 105 mN/m.

With a layer of type 1 impregnated with a 0.5% molar solution of methoxypoly(ethylene oxide) monomethacrylate, having a molecular weight of 1100 g/mol, in a 50/50 water/ethanol solvent, which is then plasma-treated, the resulting removal rate is between 0.7 and 1% and the grafting efficiency is greater than 70%.

With a layer of type 1 impregnated with a 0.5% molar solution of dimethoxypoly(ethylene oxide), having a molecular weight of 1000 g/mol, in an 80/20 water/ethanol solvent, which is then plasma-treated, the resulting removal rate is 0.76%, the CWST is 90 mN/m and the grafting efficiency is greater than 80%.

Filtration

A filtration unit (A) was produced with the following composition:
- two layers of polyester,
- two layers of type 2 grafted together with a methoxypoly(ethylene oxide) monomethacrylate having a molecular weight of 1100 g/mol,
- 26 layers of type 1 grafted together with a methoxypoly(ethylene oxide) monomethacrylate having a molecular weight of 1100 g/mol, and
- one layer of polyester.

A filtration unit (B) was produced with the following composition:
- two layers of polyester,
- one layer of type 2 grafted together with a methoxypoly(ethylene oxide) monomethacrylate having a molecular weight of 1100 g/mol,
- 25 layers of type 1 grafted together with a methoxypoly(ethylene oxide) monomethacrylate having a molecular weight of 1100 g/mol, and
- one layer of polyester.

A filtration unit (C) was produced with the following composition:
- two layers of polyester,
- one layer of type 2 grafted together with a methoxypoly(ethylene oxide) monomethacrylate having a molecular weight of 1100 g/mol,
- layers of type 1 grafted together with a dimethoxypoly(ethylene oxide) monomethacrylate having a molecular weight of 1000 g/mol, and
- one layer of polyester.

These units were used for filtering packed red blood cells obtained by centrifuging a unit of whole blood. The separation and filtration operations were carried out in a pouch system as shown in FIG. 6.

The filtrate collection pouch contains a preservative solution (SAGM, PAGSM). Prior to carrying out the filtration, the preservative solution is extemporaneously transferred through the filtration unit to the packed red blood cells, so as to pre-wet the leucodepletion medium and dilute the packed red blood cells. Filtration of the packed red blood cells together with the preservative solution can then begin.

The results obtained were averaged over 5 trial runs.

Results

TABLE 1

|  | Priming time (minutes:seconds) | Filtration time (minutes) | Number of residual leukocytes |
|---|---|---|---|
| Unit A | 1:00 | 21 | $5.03 \cdot 10^4$ |
| Unit B | 0:49 | 14.8 | $2.58 \cdot 10^5$ |
| Unit C | 1:04 | 24 | $9.3 \cdot 10^4$ |

The high CWST of the leucodepletion medium enables obtainment of shorter priming and filtration times, and pre-wetting of the filtration units during the pre-use storage thereof is no longer mandatory.

Grafting likewise improves leucodepletion, which enables a reduction in the number of layers as well as in the surface area of the leucodepletion medium, and therefore a reduction in the loss of blood components.

The invention claimed is:

1. Method for grafting a porous element for leucodepletion by adsorption and/or filtration of a biological fluid, said method comprising the steps of:
    impregnating the porous element with a solution consisting of a poly(ethylene oxide) having identical or different functional end groups as a solute and at least one of an aqueous and organic liquid as a solvent;
    polymerizing said poly(ethylene oxide) after impregnation of said porous element with said solution; and
    said polymerizing step comprising applying an ionizing treatment to the impregnated porous element so as to ensure covalent cross-linking between the poly(ethylene oxide) and said porous element.

2. Grafting method of claim 1, wherein the impregnating step comprises providing the poly(ethylene oxide) macromonomer of which at least one of the end groups is a group capable of being polymerized by an ionizing treatment.

3. Grafting method as claimed in claim 1, wherein the impregnating step comprises providing an impregnating solution containing between 0.01 and 5% by weight of poly(ethylene oxide).

4. Grafting method as claimed in claim 1, wherein the impregnating step comprises providing an impregnating solution including an aqueous solvent.

5. Grafting method as claimed in claim 1, further comprising carrying out the ionizing treatment by means of a gaseous plasma or electron beam.

6. Grafting method as claimed in claim 1, further comprising carrying out the impregnation by pad finishing with a removal rate of between 0.1% and 5% by weight of the porous element.

7. Grafting method as claimed in claim 2, wherein the polymerizable end group is an acrylate or a methacrylate.

8. Grafting method of claim 7, wherein the macromonomer is a methoxypoly(ethylene oxide) monomethacrylate.

9. Grafting method as claimed in claim 1, wherein the poly(ethylene oxide) has a molecular weight greater than or equal to 500 g/mol.

10. Grafting method of claim 9, wherein the poly(ethylene oxide) has a molecular weight of between 800 and 2000 g/mol.

* * * * *